US010842822B2

(12) United States Patent
Glicksman et al.

(10) Patent No.: US 10,842,822 B2
(45) Date of Patent: Nov. 24, 2020

(54) DIAGNOSIS AND TREATMENT OF PARKINSON'S DISEASE BASED ON IDENTIFICATION AND AMELIORATION OF LIVER DYSFUNCTION

(71) Applicant: Orig3n, Inc., Boston, MA (US)

(72) Inventors: Marcie A. Glicksman, Boston, MA (US); Nikhat F. Zaidi, Newton, MA (US); Robin Y. Smith, Boston, MA (US)

(73) Assignee: Orig3n, Inc., Boston, MA (US)

( * ) Notice: Subject to any disclaimer, the term of this patent is extended or adjusted under 35 U.S.C. 154(b) by 0 days.

(21) Appl. No.: 15/765,644

(22) PCT Filed: Oct. 5, 2016

(86) PCT No.: PCT/US2016/055411
§ 371 (c)(1),
(2) Date: Apr. 3, 2018

(87) PCT Pub. No.: WO2017/062401
PCT Pub. Date: Apr. 13, 2017

(65) Prior Publication Data
US 2018/0280443 A1    Oct. 4, 2018

Related U.S. Application Data

(60) Provisional application No. 62/237,248, filed on Oct. 5, 2015.

(51) Int. Cl.
| | | |
|---|---|---|
| *C12Q 1/68* | (2018.01) | |
| *A61K 35/407* | (2015.01) | |
| *C12N 5/071* | (2010.01) | |
| *A61K 9/00* | (2006.01) | |
| *A61K 35/15* | (2015.01) | |
| *A61K 35/33* | (2015.01) | |
| *C12Q 1/6883* | (2018.01) | |
| *G01N 33/50* | (2006.01) | |
| *A61P 25/16* | (2006.01) | |

(52) U.S. Cl.
CPC .......... *A61K 35/407* (2013.01); *A61K 9/0019* (2013.01); *A61K 35/15* (2013.01); *A61K 35/33* (2013.01); *C12N 5/067* (2013.01); *C12Q 1/6883* (2013.01); *G01N 33/5038* (2013.01); *A61P 25/16* (2018.01); *C12N 2501/12* (2013.01); *C12N 2506/115* (2013.01); *C12N 2510/00* (2013.01); *G01N 2800/2835* (2013.01); *G01N 2800/52* (2013.01)

(58) Field of Classification Search
None
See application file for complete search history.

(56) References Cited

U.S. PATENT DOCUMENTS

| | | |
|---|---|---|
| 8,048,999 B2 | 11/2011 | Yamanaka et al. |
| 2010/0129440 A1 | 5/2010 | Zhao et al. |
| 2010/0314251 A1 | 12/2010 | Goldknopf |
| 2011/0097378 A1 | 4/2011 | Badylak |
| 2011/0223669 A1 | 9/2011 | Yamanaka et al. |
| 2012/0190059 A1 | 7/2012 | Deng et al. |
| 2013/0065311 A1 | 3/2013 | Yamanaka et al. |
| 2013/0115622 A1 | 5/2013 | Inoue et al. |
| 2014/0087416 A1 | 3/2014 | Simeonov et al. |
| 2014/0249209 A1 | 9/2014 | Fox et al. |
| 2014/0302068 A1 | 10/2014 | Khoo et al. |

FOREIGN PATENT DOCUMENTS

| | | |
|---|---|---|
| EP | 2671944 A1 | 12/2013 |
| WO | WO-1995/027512 A2 | 10/1995 |
| WO | WO-02/064748 A2 | 8/2002 |
| WO | WO-2012/105505 A1 | 8/2012 |
| WO | WO 2013/036936 A1 * | 3/2013 |
| WO | WO-2014/085830 A2 | 6/2014 |
| WO | WO-2014/124527 A1 | 8/2014 |
| WO | WO-2015/003643 A1 | 1/2015 |

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Burgess, James B. et al., Abnormal Surface Distribution of the Human Asialoglycoprotein Receptor in Cirrhosis, Hepatology, 15(4):702-706, (1992).
He, Zhi-Xu et al, Impact of physiological, pathological and environmental factors on the expression and activity of human cytochrome P450 2D6 and implications in precision medicine, Drug Metabolism Reviews, 47(4):470-519, (2015).
Lai, Jun-Kai et al., Krüppel-like factor 4 is involved in cell scattering induced by hepatocyte growth factor, Journal of Cell Science 125(20):4853-4864, (2012).
Santiago, Jose A. and Potashkin, Judith A., Network-based metaanalysis identifies HNF4A and PTBP1 as longitudinally dynamic biomarkers for Parkinson's disease, PNAS, 112(7)2257-2262, (2015).
Santiago, Jose A. and Potashkin, Judith A., Reply to Toker and Pavlidis: Blood biomarkers for Parkinson's disease, PNAS 112(28)E3638, (2015).
Toker, Lilah and Pavlidis, Paul, Metaanalysis of flawed expression profiling data leading to erroneous Parkinson's biomarker identification, PNAS, 112(28):E3637, (2015).
Cai, J. et al., Directed Differentiation of Human Embryonic Stem Cells into Functional Hepatic Cells, Hepatology, 45(5):1229-1239, (2007).

(Continued)

*Primary Examiner* — James Martinell
(74) *Attorney, Agent, or Firm* — Foley Hoag LLP

(57) ABSTRACT

Disclosed are methods for diagnosing Parkinson's disease, or identifying a risk of developing Parkinson's disease, comprising measuring the amount of a biomolecule in a blood sample, liver sample, or hepatocyte. Also disclosed are methods for preventing or treating Parkinson's disease, comprising administering a therapeutically effective plurality of hepatocytes to a subject in need thereof.

9 Claims, 2 Drawing Sheets

(56) References Cited

OTHER PUBLICATIONS

Fusaki, N. et al., Efficient induction of transgene-free human pluripotent stem cells using a vector based on Sendai virus, an RNA virus that does not integrate into the host genome, Proc. Jpn. Acad., Ser. B, 85:348-362, (2009).

Huangfu, D. et al., Induction of pluripotent stem cells by defined factors is greatly improved by small-molecule compounds, Nature Biotechnology, 26(7):795-797 with Supplemental Data included, (2008).

International Search Report, PCT/US16/55411 (Diagnosis and Treatment of Parkinson's Disease Based on Identification and Amelioration of Liver Dysfunction, filed Oct. 5, 2016), issued by ISA/US, 3 pages, dated Feb. 3, 2017.

Judson, R. L. et al., Embryonic stem cell-specific microRNAs promote induced pluripotency, Nature Biotechnology, 27(5):459-461 with Supplemental Data included, (2009).

Lin, T. et al., A chemical platform for improved induction of human iPSCs, Nature Methods, 6(11):805-808 with Supplemental Data included, (2009).

Marson, A. et al., Wnt Signaling Promotes Reprogramming of Somatic Cells to Pluripotency, Cell Stem Cell, 3:132-135 with Supplemental Data included, (2008).

Nakagawa, M. et al., Generation of induced pluripotent stem cells without Myc from mouse and human fibroblasts, Nature Biotechnology, 26(1):101-106 Supplementary Data included, (2008).

Okita, K. et al., Generation of Mouse Induced Pluripotent Stem Cells Without Viral Vectors, Science, 322:949-953, (2008).

Rambhatla, L. et al., Generation of Hepatocyte-Like Cells from Human Embryonic Stem Cells, Cell Transplantation, 12:1-11, (2003).

Shi, Y. et al., A Combined Chemical and Genetic Approach for the Generation of Induced Pluripotent Stem Cells, Cell Stem Cell, 2:525-528 with Supplemental Data included, (2008).

Shi, Y. et al., Induction of Pluripotent Stem Cells from Mouse Embryonic Fibroblasts by Oct4 and Klf4 with Small-Molecule Compounds, Cell Stem Cell, 3:568-574 with Supplemental Data included, (2008).

Silva, J. et al., Promotion of Reprogramming to Ground State Pluripotency by Signal Inhibition, PLoS Biology, 6(10):e253:2237-2247, (2008).

Stadtfeld, M. et al., Induced Pluripotent Stem Cells Generated Without Viral Integration, Science, 322:945-949, (2008).

Takahashi, K. and Yamanaka S., Induction of Pluripotent Stem Cells from Mouse Embryonic and Adult Fibroblast Cultures by Defined Factors, Cell, 126:663-676 (2006).

Takahashi, K. et al., Induction of Pluripotent Stem cells from Adult Human, Fibroblasts by Defined Factors, Cell, 131:861-872 (2007).

Written Opinion, PCT/US16/55411 (Diagnosis and Treatment of Parkinson's Disease Based on Identification and Amelioration of Liver Dysfunction, filed Oct. 5, 2016), issued by ISA/US, 7 pages, dated Feb. 3, 2017.

Yu, J. et al., Induced Pluripotent Stem Cell Lines Derived from Human Somatic Cells, Science, 318:1917-1920, (2007).

Zhao, Y. et al., Two Supporting Factors Greatly Improve the Efficiency of Human iPSC Generation, Cell Stem Cell, 3:475-479 with Supplemental Data included, (2008).

\* cited by examiner

DIAGNOSIS AND TREATMENT OF PARKINSON'S DISEASE BASED ON IDENTIFICATION AND AMELIORATION OF LIVER DYSFUNCTION

CROSS-REFERENCE TO RELATED APPLICATION

This application claims the benefit of priority to U.S. Provisional Application Ser. No. 62/237,248, filed Oct. 5, 2015, which is hereby incorporated by reference in its entirety.

BACKGROUND

Parkinson's disease is a movement disorder of increasing occurrence in aging populations. It is a common disabling disease of old age, affecting about 1% of the population over the age of 60 in the United States. The incidence of Parkinson's disease increases with age and the cumulative lifetime risk of an individual developing the disease is about 1 in 40. Symptoms include pronounced tremor of the extremities, bradykinesia, rigidity and postural change. A postulated pathophysiological cause of Parkinson's disease is progressive destruction of dopamine producing cells in the basal ganglia which comprise the pars compartum of the substantia nigra, a basal nuclei located in the brain stem.

Parkinson's disease is a progressive disorder which can begin with mild limb stiffness and infrequent tremors and progress over a period of ten or more years to frequent tremors and memory impairment, to uncontrollable tremors and dementia.

Research for the cause of the disease has mostly been in the areas of altered genetics and altered neuronal function. Currently, there are no laboratory tests available for Parkinson's disease, so the disease is diagnosed based on clinical symptoms.

There is no known cure for Parkinson's disease. The available medications prescribed to patients diagnosed with Parkinson's disease can relieve some of their symptoms. Several medications consist of precursors to dopamine. The precursors are taken up by neurons and converted to dopamine to supplement the lowered amounts of dopamine in the brain. At later stages of the disease, this symptomatic therapy is typically no longer effective. Thus, a strong need for new therapeutics exists.

SUMMARY

In some aspects, the invention relates to a method for diagnosing Parkinson's disease. In some aspects, the invention relates to a method for identifying a risk of developing Parkinson's disease. In certain embodiments, the method comprises providing a blood sample taken from a subject, a liver sample taken from the subject, or a hepatocyte, wherein said hepatocyte is generated from a non-hepatocyte cell taken from the subject and then differentiated into the hepatocyte. In certain embodiments, the method comprises measuring the amount of a biomolecule in the blood sample, the liver sample, or the hepatocyte. The method may comprise diagnosing the subject as having Parkinson's disease, for example, if the measured amount of the biomolecule is comparable to an amount present in a blood sample taken from an individual diagnosed with Parkinson's disease, a liver sample taken from the individual diagnosed with Parkinson's disease, or a hepatocyte, wherein said hepatocyte is derived from a non-hepatocyte cell taken from the individual diagnosed with Parkinson's disease and then differentiated into the hepatocyte. The method may comprise identifying the subject as at risk of developing Parkinson's disease, for example, if the measured amount of the biomolecule is comparable to an amount present in a blood sample taken from an individual diagnosed with Parkinson's disease, a liver sample taken from the individual diagnosed with Parkinson's disease, or a hepatocyte, wherein said hepatocyte is derived from a non-hepatocyte cell taken from the individual diagnosed with Parkinson's disease and then differentiated into the hepatocyte. The biomolecule may be, for example, a protein or RNA molecule.

In some aspects, the invention relates to a method for identifying a therapeutic agent for treating Parkinson's disease. The method may comprise contacting a first hepatocyte with a compound or composition, and measuring the amount of a biomolecule produced by the first hepatocyte. The method may comprise comparing the amount of the biomolecule produced by the first hepatocyte with an amount of the biomolecule produced by a control hepatocyte. The method may comprise identifying the compound or composition as a therapeutic agent for treating Parkinson's disease if the amount of the biomolecule produced by the first hepatocyte is different from the amount of the biomolecule produced by the control hepatocyte. For example, the first hepatocyte and control hepatocyte may have genotypes and/or phenotypes that are consistent with Parkinson's disease, and identifying a compound or composition as a therapeutic agent for treating Parkinson's disease may comprise identifying a difference between the amount of the biomolecule produced by the first hepatocyte and the amount of the biomolecule produced by the control hepatocyte, wherein the first hepatocyte produces an amount of the biomolecule similar to the amount produced by a healthy hepatocyte and different to the amount produced by the control hepatocyte. Identifying the compound or composition as a therapeutic agent for treating Parkinson's disease may comprise identifying a shift in the amount of the biomolecule produced by the first hepatocyte away from the amount of the biomolecule produced by the control hepatocyte, i.e., wherein the shift is toward the amount of the biomolecule that a healthy hepatocyte would produce. The biomolecule may be, for example, a protein or RNA.

Similarly, the first hepatocyte may have a genotype and/or phenotype that is consistent with Parkinson's disease and the control hepatocyte may have a non-Parkinson's genotype and/or phenotype, and identifying a compound or composition as a therapeutic agent for treating Parkinson's disease may comprise identifying a decrease in the amount of a biomolecule produced by the first hepatocyte. Thus, identifying the compound or composition as a therapeutic agent for treating Parkinson's disease may comprise identifying a shift in the amount of the biomolecule produced by the first hepatocyte toward the amount of the biomolecule produced by the control hepatocyte, i.e., wherein the shift is away from the amount of the biomolecule produced by the first hepatocyte before contacting the first hepatocyte with the compound or composition. The biomolecule may be, for example, a protein or RNA.

In some aspects, the invention relates to a method for preventing or treating Parkinson's disease comprising administering a therapeutically effective plurality of hepatocytes to a subject in need thereof.

DETAILED DESCRIPTION

Figure 1:
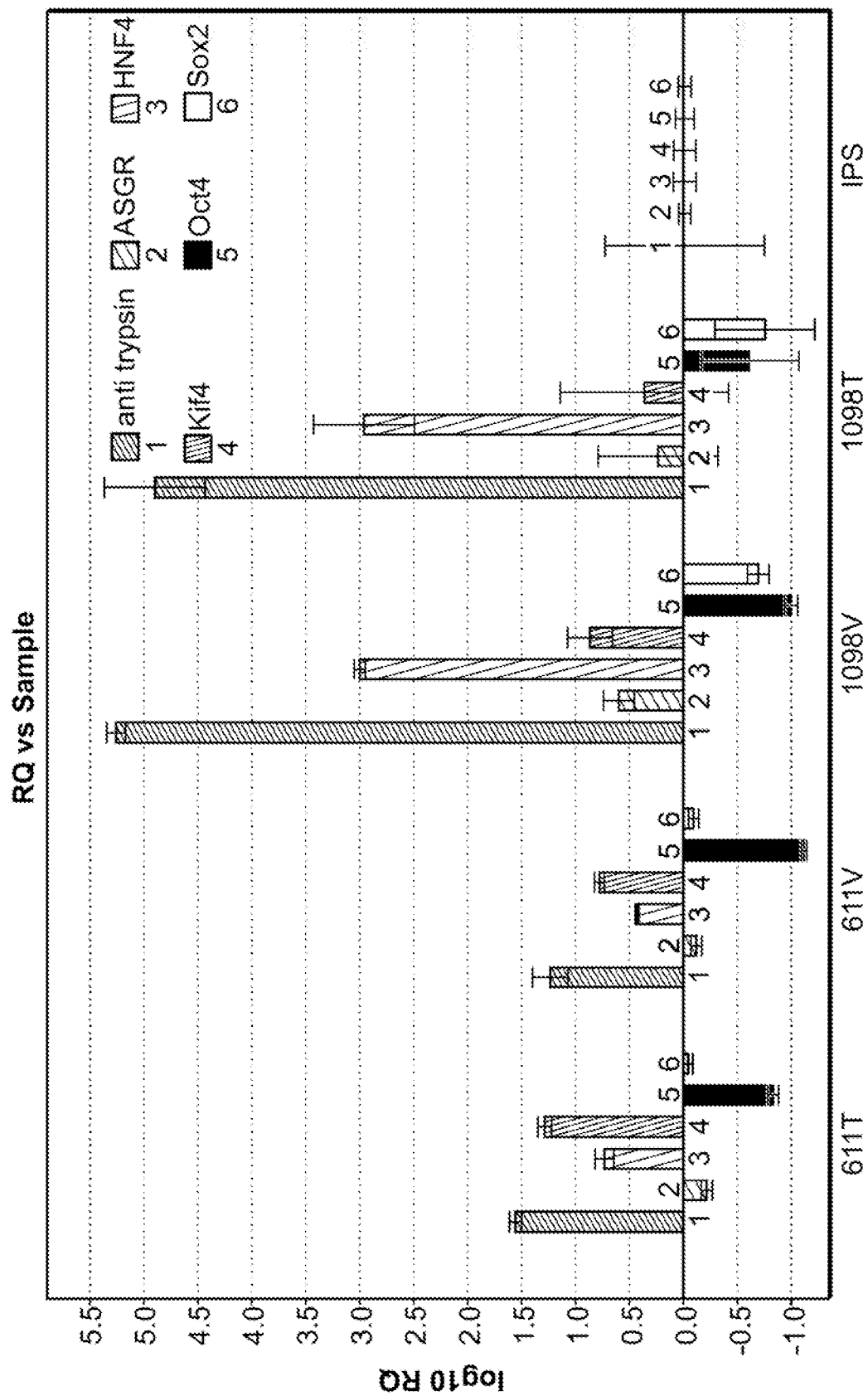
FIG. 1 shows gene expression analysis of characteristic hepatic markers in differentiated hepatocytes from control human sample (1098) and Parkinson's patient sample (611). Specific hepatic markers (Anti trypsin, HNF4 and ASGR) mRNA were measured using qRT-PCR. Each marker was normalized to GAPDH and relative change was expressed compared to parental human IPS cell line. The pluripotency genes Oct4 and Sox2 were significantly down-regulated.

Aspects of the invention relate to the finding that hepatocytes derived from certain Parkinson's disease patients vary from healthy individuals, and thus, hepatocyte dysfunction may play a role in the onset and progression of Parkinson's disease. Specifically, Parkinson's disease patients have hepatocytes that lack proper function and express abnormal levels of identifying markers. For example, Parkinson's disease hepatocytes express lower levels of albumin than hepatocytes from healthy individuals, and other genes associated with mature hepatocytes, such as trypsin, Hepatocyte Nuclear Factor 4 (HNF4), and asialoglycoprotein receptor (ASGR), are expressed at lower levels in hepatocytes derived from Parkinson's disease patients than from healthy controls.

I. Methods Related to Diagnosing Parkinson's Disease

In some aspects, the invention relates to a method for diagnosing Parkinson's disease. In some aspects, the invention relates to a method for identifying a risk of developing Parkinson's disease. In certain embodiments, the method comprises providing a blood sample taken from a subject, a liver sample taken from the subject, or a hepatocyte, wherein said hepatocyte is generated from a non-hepatocyte cell taken from the subject and then differentiated into the hepatocyte. In certain embodiments, the method comprises measuring the amount of a biomolecule in the blood sample, the liver sample, or the hepatocyte. The method may comprise diagnosing the subject as having Parkinson's disease, for example, if the measured amount of the biomolecule is comparable to an amount present in a blood sample taken from an individual diagnosed with Parkinson's disease, a liver sample taken from the individual, or a hepatocyte, wherein said hepatocyte is derived from a non-hepatocyte cell taken from the individual and then differentiated into the hepatocyte. The method may comprise identifying the subject as at risk of developing Parkinson's disease if the measured amount of the biomolecule is comparable to an amount present in a blood sample taken from an individual diagnosed with Parkinson's disease, a liver sample taken from the individual, or a hepatocyte, wherein said hepatocyte is derived from a non-hepatocyte cell taken from the individual and then differentiated into the hepatocyte.

The method may comprise diagnosing the subject as not having Parkinson's disease, for example, if the measured amount of the biomolecule is comparable to an amount present in a blood sample taken from a healthy individual, a liver sample taken from the individual, or a hepatocyte, wherein said hepatocyte is derived from a non-hepatocyte cell taken from the individual and then differentiated into the hepatocyte. The method may comprise identifying the subject as low risk for developing Parkinson's disease if the measured amount of the biomolecule is comparable to an amount present in a blood sample taken from a healthy individual, a liver sample taken from the individual, or a hepatocyte, wherein said hepatocyte is derived from a non-hepatocyte cell taken from the individual and then differentiated into the hepatocyte.

The biomolecule may be, for example, a protein or RNA.

In certain embodiments, the subject is human. The subject may present with at least one symptom of Parkinson's disease, such as tremor, hypokinesia, rigidity, postural instability, or a neuropsychiatric disturbance, such as dementia. The subject may be diagnosed with Parkinson's disease. In some embodiments, the subject dose not present with a symptom of Parkinson's disease and the subject has not been diagnosed with Parkinson's disease. In some embodiments, the subject has at least one relative with Parkinson's disease, i.e., wherein the relative and the subject share inheritable genotypes. For example, the subject may be a descendant of a person who has or had Parkinson's disease. The subject may have a mutation that is known to correlate with Parkinson's disease, such as a mutation to alpha-synuclein (SNCA), parkin (PRKN), leucine-rich repeat kinase 2 (LRRK2), PTEN-induced putative kinase 1 (PINK1), DJ-1, glucocerebrosidase, or ATP13A2. In some embodiments, the subject does not have a relative who is known to have Parkinson's disease. In some embodiments, the subject has detectable Lewy bodies. In some embodiments, the subject is substantially free of detectable Lewy bodies.

In some embodiments, the method comprises providing a hepatocyte, wherein said hepatocyte is generated from a stem cell, e.g., a pluripotent stem cell, such as an induced pluripotent stem cell.

In some embodiments, the method comprises providing a hepatocyte, wherein said hepatocyte is generated from a non-hepatocyte cell taken from the subject and then differentiated into the hepatocyte. Generating the hepatocyte from a non-hepatocyte cell may comprise generating a pluripotent stem cell from the cell and differentiating the pluripotent stem cell into a hepatocyte, thereby generating the hepatocyte. The cell may be, for example, a peripheral blood mononuclear cell or a fibroblast.

Generating the pluripotent stem cell from the cell may comprise transducing the cell with a gene for Kruppel-like factor 4 (Klf4), octamer-binding transcription factor 3/4 (Oct-3/4), octamer-binding transcription factor 4 (Oct-4), SRY (sex determining region Y)-box 2 (Sox2), and/or c-Myc. Generating a pluripotent stem cell may comprise transducing the cell with a gene for Oct3/4, Oct4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Glisl, Esrrb, and/or Esrrg. Transducing the cell may comprise transducing the cell with at least one vector, e.g., wherein the at least one vector comprises a gene for Klf4, Oct-3/4, Oct-4, Sox2, and/or c-Myc. The vector may be, for example, a plasmid vector or a viral vector, such as a Sendai virus vector. Transducing the cell may comprise transducing the cell with at least one Sendai virus vector, e.g., wherein the at least one Sendai virus vector comprises a gene for Klf4, Oct-3/4, Oct-4, Sox2, and/or c-Myc. Methods for generating pluripotent stem cells from a cell are well known in the art, and include those described in U.S. Patent Application Publication Nos. 2011/0223669 and 2013/0065311, each of which is hereby incorporated by reference. Methods for generating pluripotent stem cells from somatic cells using small molecules rather than nucleic acids are also known in the art (see, e.g., PCT Patent Application Publication No. WO 2015/003643, hereby incorporated by reference).

Differentiating the pluripotent stem cell into the hepatocyte may comprise differentiating the pluripotent stem cell into an endoderm cell, e.g., by incubating the pluripotent stem cell in endoderm media. Differentiating the pluripotent stem cell into the hepatocyte may comprise incubating the pluripotent stem cell or endoderm cell in media (e.g., serum free media) comprising bone morphogenic protein 4 (BMP-4) and/or fibroblast growth factor 2 (FGF-2). Differentiating the pluripotent stem cell into the hepatocyte may comprise incubating the pluripotent stem cell or endoderm cell in media (e.g., serum free media) comprising human growth factor (HGF). Differentiating the pluripotent stem cell into the hepatocyte may comprise incubating the pluripotent stem cell or endoderm cell in media (e.g., serum free media) comprising oncostatin. Other methods of differentiating pluripotent stem cells into hepatocytes are well known in the art (see, e.g., U.S. Patent Application Publication No. 2012/0190059, hereby incorporated by reference).

The blood sample, liver sample, or non-hepatocyte cell may be obtained directly from the subject, e.g., by drawing the blood of the subject, performing a liver biopsy, or by another means, such as a skin biopsy. The blood sample, liver sample, or non-hepatocyte cell may be obtained indirectly from the subject. For example, the sample or cell may be obtained from a health care provider of the subject, e.g., through the mail. The sample or cell may be obtained from a blood or tissue bank or other archive.

The biomolecule may be albumin or an RNA encoding albumin. The biomolecule may be antitrypsin, asialoglycoprotein receptor, or hepatocyte nuclear factor 4, or an RNA encoding antitrypsin, asialoglycoprotein receptor, or hepatocyte nuclear factor 4. The biomolecule may be cytochrome P450IID6, cytochrome P450MP, cytochrome P450PA, cysteine dioxygenase, or an RNA encoding cytochrome P450IID6, cytochrome P450MP, cytochrome P450PA, or cysteine dioxygenase.

In some embodiments, the biomolecule is RNA, and the amount of the biomolecule is measured by PCR, microarray analysis, or sequencing.

In some embodiments, the biomolecule is a peptide or protein, and the amount of the biomolecule is measured using flow cytometry, magnetic-activated cell sorting, or an immunoassay (e.g., ELISA).

The method may further comprise administering an agent to the subject (i.e., a subject who is diagnosed with Parkinson's disease or who displays a risk of developing Parkinson's disease) to prevent, delay the onset of, or treat Parkinson's disease. The method may further comprise administering an agent to the subject (i.e., a subject who is diagnosed with Parkinson's disease or who displays a risk of developing Parkinson's disease) to prevent, delay the onset of, or treat one or more symptoms of Parkinson's disease. The agent may be, for example, levodopa.

II. Methods Related to Identifying Therapeutic Agents for Treating Parkinson's Disease In some aspects, the invention relates to a method for identifying a therapeutic agent for treating Parkinson's disease. The method may comprise contacting a first hepatocyte with a compound or composition and measuring the amount of a biomolecule produced by the first hepatocyte. The method may comprise comparing the amount of the biomolecule produced by the first hepatocyte with an amount of the biomolecule produced by a control hepatocyte. The method may comprise identifying the compound or composition as a therapeutic agent for treating Parkinson's disease if the amount of the biomolecule produced by the first hepatocyte is different from the amount of the biomolecule produced by the control hepatocyte. For example, the first hepatocyte and control hepatocyte may have genotypes and/or phenotypes that are consistent with Parkinson's disease, and identifying a compound or composition as a therapeutic agent for treating Parkinson's disease may comprise identifying a difference between the amount of the biomolecule produced by the first hepatocyte and the amount of the biomolecule produced by the control hepatocyte, wherein the first hepatocyte produces an amount of the biomolecule that is more similar to a healthy hepatocyte than the control hepatocyte. Thus, identifying the compound or composition as a therapeutic agent for treating Parkinson's disease may comprise identifying a shift in the amount of the biomolecule produced by the first hepatocyte away from the amount of the biomolecule produced by the control hepatocyte, i.e., wherein the shift is toward the amount of the biomolecule that a healthy hepatocyte would produce.

Similarly, the first hepatocyte may have a genotype and/or phenotype that is consistent with Parkinson's disease and the control hepatocyte may have a non-Parkinson's genotype and/or phenotype, and identifying a compound or composition as a therapeutic agent for treating Parkinson's disease may comprise identifying that the amount of a biomolecule produced by the first hepatocyte is more similar to the amount of the biomolecule produced by the control hepatocyte than the amount of the biomolecule produced by the first hepatocyte prior to contacting the first hepatocyte with the compound or composition. Thus, identifying the compound or composition as a therapeutic agent for treating Parkinson's disease may comprise identifying a shift in the amount of the biomolecule produced by the first hepatocyte toward the amount of the biomolecule produced by the control hepatocyte, i.e., wherein the shift is away from the amount of the biomolecule produced by the first hepatocyte before contacting the first hepatocyte with the compound or composition.

The biomolecule may be, for example, a protein or RNA.

The first hepatocyte may be derived from a cell line, e.g., an immortalized cell line, that has a genotype and/or phenotype that is associated with Parkinson's disease. The first hepatocyte may be derived from a cell line obtained from a subject who has a genotype and/or phenotype that is associated with Parkinson's disease. The first hepatocyte may be derived from a cell line obtained from a subject who has Parkinson's disease.

The control hepatocyte may be derived from a cell line, e.g., an immortalized cell line, that has a genotype and/or phenotype that is associated with Parkinson's disease. The first hepatocyte and the control hepatocyte may be derived from the same cell line. The control hepatocyte may be derived from a cell line obtained from a subject who has a genotype and/or phenotype that is associated with Parkinson's disease. The first hepatocyte and the control hepatocyte may be derived from the same subject. The control hepatocyte may be derived from a cell line obtained from a subject who has Parkinson's disease. The first hepatocyte and the control hepatocyte may be derived from the same cell line.

The control hepatocyte may be derived from a cell line, e.g., an immortalized cell line, that has a healthy genotype and/or phenotype, e.g., that is not associated with Parkinson's disease. The control hepatocyte may be derived from a cell line obtained from a healthy subject, e.g., who has a genotype and/or phenotype that is not associated with Parkinson's disease. The control hepatocyte may be derived from a cell line obtained from a healthy subject, e.g., who does not have Parkinson's disease.

The first hepatocyte may be a hepatocyte from a subject who has a genotype and/or phenotype that is associated with Parkinson's disease. The first hepatocyte may be a hepatocyte from a subject who has Parkinson's disease.

The control hepatocyte may be a hepatocyte from a subject who has a genotype and/or phenotype that is associated with Parkinson's disease. The control hepatocyte may be a hepatocyte from a subject who has Parkinson's disease. The first hepatocyte and the control hepatocyte may be from the same subject.

The control hepatocyte may be a hepatocyte from a healthy subject, e.g., who has a genotype and/or phenotype that is not associated with Parkinson's disease. The control hepatocyte may be a hepatocyte from a subject who does not have Parkinson's disease.

The first hepatocyte and/or control hepatocyte may be derived from a pluripotent stem cell, e.g. a pluripotent stem cell from a subject who has a genotype and/or phenotype that is associated with Parkinson's disease. For example, the first hepatocyte may be derived from a pluripotent stem cell from a subject who has Parkinson's disease. The pluripotent stem cell may be a pluripotent stem cell that is obtained from a subject (e.g., a subject with Parkinson's disease), or the pluripotent stem cell may be generated from a differentiated cell obtained from a subject (e.g., a subject with Parkinson's disease), such as a peripheral blood mononuclear cell or a fibroblast. The control hepatocyte may be derived from a pluripotent stem cell either from a subject who has Parkinson's disease or from a healthy subject. A pluripotent stem cell may be generated by any method, including any method disclosed herein. A hepatocyte may be generated by any method, including any method disclosed herein.

In certain embodiments, the first hepatocyte is a human hepatocyte, i.e., the first hepatocyte comprises a human genome. In certain embodiments, the control hepatocyte is a human hepatocyte, i.e., the control hepatocyte comprises a human genome. In certain embodiments, the first hepatocyte and the control hepatocyte comprise genomes of the same species (e.g., each genome is a human genome).

The compound may be a small molecule or a biologic. For example, the compound may be a small molecule, and the small molecule may have a molecular weight of about 200 amu to about 5000 amu, such as about 300 amu to about 2000 amu, or about 400 amu to about 1000 amu. The compound may be a biologic, and the biologic may have a molecular weight of about 1000 amu to about 500,000 amu, such as about 5000 amu to about 200,000 amu, such as about 5,000 amu to about 10,000 amu, about 10,000 amu to about 25,000 amu, about 25,000 amu to about 75,000 amu, about 75,000 amu to about 125,000 amu, or about 125,000 amu to about 175,000 amu. In some embodiments, the compound is a biologic, and the biologic is a nucleic acid, e.g., RNA or DNA, or a protein, e.g., a peptide or polypeptide. In some embodiments, the compound is an antibody or a fragment of an antibody (i.e., a protein). In some embodiments, the compound comprises an antibody or a fragment of an antibody (i.e., a protein). The compound may be, for example, a single-domain antibody or the Fab fragment of an antibody. The compound may be a small interfering RNA. The compound may be, for example, a plasmid encoding CRISPR/Cas and guide RNAs. The compound may be a zinc finger nuclease or a nucleic acid encoding a zinc finger nuclease. The compound may be a transcription activator-like effector nuclease (TALEN), or a nucleic acid encoding a TALEN. The compound may be a nucleic acid encoding albumin.

In some embodiments, the hepatocyte is contacted with a composition. The composition may comprise a compound as described herein, such as a biologic. The composition may comprise a mixture for CRISPR-mediated editing of a gene. Similarly, the composition may comprise a mixture for zinc finger nuclease- or TALEN-mediated editing of a gene. The composition may comprise a gene therapy vector, such as a viral vector.

III. Methods Related to Treating Parkinson's Disease

In some aspects, the invention relates to a method for preventing or treating Parkinson's disease comprising administering a therapeutically effective plurality of hepatocytes to a subject in need thereof.

The plurality of hepatocytes may comprise hepatocytes that have a genome that is associated with Parkinson's disease (i.e., hepatocytes comprising the genome of the subject), e.g., wherein hepatocyte has been modified to display a phenotype that is more similar to a healthy phenotype than an unmodified hepatocyte with the same genome.

The plurality of hepatocytes may comprise hepatocytes that do not comprise a Parkinson's phenotype. In some embodiments, each hepatocyte of the plurality of hepatocytes comprises a healthy phenotype. In some embodiments, none of the hepatocytes of the plurality of hepatocytes comprises a Parkinson's phenotype.

In some embodiments, the hepatocytes of the plurality of hepatocytes produce more albumin than hepatocytes that have a Parkinson's disease phenotype.

In some embodiments, the hepatocytes of the plurality of hepatocytes produce more antitrypsin, asialoglycoprotein receptor, or hepatocyte nuclear factor 4 than hepatocytes that have a Parkinson's disease phenotype. In some embodiments, the hepatocytes of the plurality of hepatocytes produce more cytochrome P45011D6, cytochrome P450MP, cytochrome P450PA, or cysteine dioxygenase than hepatocytes that have a Parkinson's disease phenotype.

In certain embodiments, the hepatocytes of the plurality of hepatocytes are derived from cells taken from the subject, preferably somatic cells, such as diploid cells.

In some embodiments, the genomes of the hepatocytes have been edited, e.g., by a CRISPR/Cas, zinc finger nuclease, or transcription activator-like effector nuclease. For example, the hepatocytes of the plurality of hepatocytes may be derived from cells taken from the subject (i.e., a subject with a genotype that is associated with Parkinson's disease), and the genomes of the hepatocytes may be edited such that the hepatocytes display a phenotype that is more like a healthy hepatocyte than a Parkinson's disease hepatocyte.

In some embodiments, the hepatocytes are derived from cells taken from the subject. The hepatocytes may be derived from pluripotent stem cells, e.g., pluripotent stem cells taken from the subject. The hepatocytes may be derived from pluripotent stem cells and the pluripotent stem cells may be derived from one or more differentiated cells taken from the subject, such as blood mononuclear cells or fibroblasts. In some embodiments, the hepatocytes are not derived from cells taken from the subject.

In certain embodiments, the hepatocytes of the plurality of hepatocytes are not derived from cells taken from the subject. The hepatocytes may be derived, for example, from cells taken from an allogeneic donor.

In some embodiments, the hepatocytes are administered by insertion into the liver of the subject. For example, the hepatocytes may be inserted into the hepatic portal vein of the subject. Inserting the cells may comprise implanting the cells, such as by surgically implanting the cells. Inserting the cells may comprise injecting the cells, e.g., by injecting the cells into the liver or into the hepatic portal vein.

In some aspects, the invention relates to a method for preventing or treating Parkinson's disease comprising administering a therapeutically effective plurality of cells to a subject in need thereof, wherein the cells are hepatocytes or the cells are capable of differentiating into hepatocytes. The method may comprise any one of the methods described herein for administering hepatocytes to a subject, e.g., and vary only in that the cells are not fully-differentiated hepatocytes. Nevertheless, the cells may be capable of being differentiated into hepatocytes, e.g., after administering the cells to the subject. Thus, the method may comprise administering a therapeutically effective plurality of stem cells to a subject. The stem cells may express, for example, at least one hepatocyte progenitor cell marker or at least one mature hepatocyte marker. In some embodiments, the stem cells are pluripotent stem cells, e.g., and the stem cells do not express a hepatocyte progenitor cell marker or a mature hepatocyte marker.

In certain embodiments, the subject is a mammal, such as a murine or primate. The subject may be a mouse. In some embodiments, the subject is a human.

The subject may present with at least one symptom of Parkinson's disease, such as tremor, hypokinesia, rigidity, postural instability, or a neuropsychiatric disturbance, such as dementia. The subject may be diagnosed with Parkinson's disease. In some embodiments, the subject dose not present with a symptom of Parkinson's disease and the subject has not been diagnosed with Parkinson's disease. In some embodiments, the subject has at least one relative with Parkinson's disease, i.e., wherein the relative and the subject share inheritable genotypes. For example, the subject may be a descendant of a person who has or had Parkinson's disease. The subject may have a mutation that is known to correlate with Parkinson's disease, such as a mutation to alpha-synuclein (SNCA), parkin (PRKN), leucine-rich repeat kinase 2 (LRRK2), PTEN-induced putative kinase 1 (PINK1), DJ-1, glucocerebrosidase, or ATP13A2. In some embodiments, the subject does not have a relative who is known to have Parkinson's disease. In some embodiments, the subject has detectable Lewy bodies. In some embodiments, the subject is substantially free of detectable Lewy bodies.

IV. Methods for Producing Pluripotent Stem Cells

An induced pluripotent stem cell (iPS cell) is an artificial stem cell derived from a somatic cell, which has nearly the same characteristics as those of embryonic stem cells (ES cell), such as differentiation pluripotency and the potential for proliferation by self-renewal. iPS cells may be prepared by transferring a certain nuclear reprogramming substance, in the form of nucleic acid or protein, to a somatic cell (see, e.g., K. Takahashi and S. Yamanaka (2006) Cell, 126: 663-676; K. Takahashi et al. (2007) Cell, 131: 861-872; J. Yu et al. (2007) Science, 318: 1917-1920; M. Nakagawa et al. (2008) Nat. Biotechnol., 26: 101-106; PCT Patent Application Publication Nos. WO2007/069666; WO2011/074690, and U.S. Patent Application Publication Nos. 2011/0223669 and 2013/0065311, each of which are hereby incorporated by reference). The nuclear reprogramming substance may be any gene specifically expressed in ES cells, or a gene that plays a key role in the maintenance of the undifferentiated state of ES cells, or a gene product thereof. Examples include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmil, Lin28, Lin28b, Nanog, Esrrb and Esrrg. These reprogramming substances may be used in combination when establishing iPS cells. For example, a combination comprising at least one, two or three of these reprogramming substances may be used, with preference given to a combination comprising four.

These nuclear reprogramming substances may be transferred to somatic cells in the form of a protein by means of, for example, lipofection, binding to cell membrane permeable peptides, and microinjection, or may be transferred to somatic cells in the form of DNA by means of, for example, vectors such as viruses, plasmids, and artificial chromosomes, as well as lipofection, liposomes, and microinjection. Examples of viral vectors include retrovirus vectors, lentivirus vectors (Cell 126:663-676 (2006); Cell 131:861-872 (2007); Science 318:1917-1920 (2007), each of which is hereby incorporated by reference), adenovirus vectors (Science 322:945-949 (2008), hereby incorporated by reference), adeno-associated virus vectors, Sendai virus vectors (Proc. Jpn. Acad. Ser. B. Phys. Biol. Sci. 85:348-62 (2009), hereby incorporated by reference) and the like. Artificial chromosomal vectors include, for example, human artificial chromosome (HAC), yeast artificial chromosome (YAC), bacterial artificial chromosome (BAC, PAC) and the like. Plasmids for mammalian cells can be used (Science 322: 949-953 (2008), hereby incorporated by reference). The vector can contain a regulatory sequence such as a promoter, enhancer, ribosome-binding sequence, terminator, or polyadenylation site to allow a nuclear reprogramming substance to be expressed, and can further contain, as required, a drug resistance gene (e.g., kanamycin resistance gene, ampicillin resistance gene, puromycin resistance gene and the like), a selection marker sequence such as the thymidine kinase gene or diphtheria toxin gene, a reporter gene sequence such as of green fluorescent protein (GFP), β glucuronidase (GUS) or FLAG, and the like. The vector may have a loxP sequence placed at both ends of the gene that encodes the nuclear reprogramming substance or of a promoter and the gene connected thereto, to enable resection thereof, after being transferred to somatic cells. The vector may also contain the EBNA-1 and oriP sequences or the Large T and SV40ori sequences to allow the vector to be replicated and occur episomally even without being incorporated in the chromosome.

Other factors may be used to increase iPS cell induction efficiency in nuclear reprogramming, in addition to the above-described factors. For example, histone deacetylase (HDAC) inhibitors {e.g., valproic acid (VPA) (*Nat. Biotechnol.*, 26(7):795-797 (2008), hereby incorporated by reference)}, low-molecular inhibitors such as trichostatin A, sodium butyrate, MC 1293, and M344, nucleic acid-based expression inhibitors such as siRNAs and shRNAs against HDAC {e.g., HDAC1 siRNA Smartpool® (Millipore), HuSH 29mer shRNA constructs against HDAC1 (OriGene), and the like}, DNA methyltransferase inhibitors (e.g., 5'-azacytidine) (*Nat. Biotechnol.*, 26(7):795-797 (2008), hereby incorporated by reference), G9a histone methyltransferase inhibitors {e.g., low-molecular inhibitors such as BIX-01294 (*Cell Stem Cell*, 2:525-528 (2008), hereby incorporated by reference), nucleic acid-based expression inhibitors such as siRNAs and shRNAs against G9a (e.g., G9a siRNA (human) (Santa Cruz Biotechnology)) and the like}, L-channel calcium agonists (e.g., Bayk8644) (*Cell Stem Cell*, 3:568-574 (2008), hereby incorporated by reference), p53 inhibitors {e.g., siRNA and shRNA against p53 (*Cell Stem Cell*, 3, 475-479 (2008), hereby incorporated by reference)}, Wnt Signaling (e.g., soluble Wnt3a) (*Cell Stem Cell*, 3, 132-135 (2008), hereby incorporated by reference), cytokines such as LIF, bFGF etc., ALK5 inhibitors (e.g., SB431542) (Nat Methods, 6:805-8 (2009), hereby incorporated by reference), a mitogen-activated protein kinase signaling inhibitor, a glycogen synthase kinase-3 inhibitor (PloS Biology, 6(10), 2237-2247 (2008), hereby incorporated by reference), miRNAs such as miR-291-3p, miR-294, and miR-295 (R. L. Judson et al., Nat. Biotech., 27:459-461 (2009), hereby incorporated by reference), and the like can be used.

Examples of culture media for iPS cell induction include (1) a DMEM, DMEM/F12 or DME medium containing 10 to 15% FBS (these media can further contain LIF, penicillin/streptomycin, puromycin, L-glutamine, non-essential amino acids, β-mercaptoethanol and the like), (2) an ES cell culture medium containing bFGF or SCF, for example, a mouse ES cell culture medium (e.g., TX-WES medium, Thromb-X NV) or a primate ES cell culture medium (e.g., primate (human and monkey) ES cell culture medium, ReproCELL, Kyoto, Japan), and the like.

In a culture method, for example, somatic cells and a nuclear reprogramming substance (DNA or protein) may be brought into contact with each other on a DMEM or DMEM/F12 medium containing 10% FBS and cultured at 37° C. in the presence of 5% $CO_2$ for about 4 to about 7 days, after which the cells may be re-seeded onto feeder cells (e.g., STO cells, SNL cells and other cells, previously treated with mitomycin C), and again cultured using a bFGF-containing primate ES cell culture medium, starting about 10 days after contact of the somatic cells and the nuclear reprogramming substance, whereby iPS-like colonies can be produced in about 30 to about 45 days or more after the contact. To increase the efficiency of iPS cell induction, the somatic cells may be cultured under conditions involving a low oxygen concentration of 5-10%.

Alternatively, the cells may be cultured on feeder cells (e.g., STO cells, SNL cells and other cells, previously treated with mitomycin C), using a DMEM medium containing 10% FBS (this can further contain LIF, penicillin/streptomycin, puromycin, L-glutamine, non-essential amino acids, β-mercaptoethanol and the like), whereby ES-like colonies can be produced after about 25 to about 30 days or more.

During the period of cultivation, the medium may be replaced with a fresh supply of the same medium once daily starting on day 2 of cultivation. Although the number of somatic cells used for nuclear reprogramming is not subject to limitations, the number may fall in the range of about $5 \times 10^3$ to about $5 \times 10^6$ cells per 100 cm$^2$ of culture dish.

When a drug resistance gene is used as a marker gene, cells that express the marker gene can be selected by cultivation using a medium containing the corresponding drug (selection medium). Cells that express the marker gene can be detected by making an observation using a fluorescence microscope for a fluorescent protein gene as the marker gene, by adding a luminescent substrate for a luminescent enzyme gene as the marker gene, and by adding a color developing substrate for a color developing enzyme gene as the marker gene.

Any cells, other than germ cells, of mammalian origin (e.g., humans, mice, monkeys, pigs, rats and the like) can be used as the "cells" of the invention. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., rod cells), autonomic neurons (e.g., cholinergic neurons), sustentacular cells of sensory organs and peripheral neurons (e.g., satellite cells), neurons and glia cells in the central nervous system (e.g., astroglia cells), pigment cells (e.g., retinal pigment epithelial cells), progenitor cells (tissue progenitor cells) thereof and the like. There is no limitation on the degree of cell differentiation, the age of the animal from which cells are collected and the like; even undifferentiated progenitor cells (including somatic stem cells) and finally differentiated mature cells can be used alike as sources of cells in the present invention.

In the present invention, the choice of mammalian individual from which somatic cells are collected is not particularly limited, but it is preferably a human. In various embodiments of the invention, it is desirable that the somatic cells be collected from a patient with Parkinson's disease or a healthy person having a genetic polymorph that correlates with the disease.

V. Methods for Differentiating Stem Cells into Hepatocytes

Methods for differentiating stem cells into hepatocytes are well known in the art (see, e.g., PCT Patent Application Publication No. WO 2012/105505, hereby incorporated by reference). Hepatocytes or hepatic stem cells may be differentiated from iPS cells. For example, culturing iPS cells in the presence of sodium butyrate may generate hepatocytes (see, e.g., Rambhatla et al. (2003) Cell Transplant 12:1-11, hereby incorporated by reference). In another example, hepatocytes may be produced by culturing iPS cells in serum-free medium in the presence of Activin A, followed by culturing the cells in fibroblast growth factor-4 and bone morphogenetic protein-2 (e.g., Cai et al. (2007) Hepatology 45(5):1229-39, hereby incorporated by reference). In another exemplary embodiment, iPS cells are differentiated into hepatic cells or hepatic stem cells by culturing iPS cells in the presence of Activin A from about 2 to about 6 days, e.g., about 2, about 3, about 4, about 5, or about 6 days, and then culturing the iPSCs in the presence of hepatocyte growth factor (HGF) for from about 5 days to about 10 days, e.g., about 5, about 6, about 7, about 8, about 9, or about 10 days.

EXEMPLIFICATION

Example 1. Harvesting Peripheral Blood Mononuclear Cells

A 12 mL LeucoSep™ tube was filled with 3 mL LeucoSep™ separation medium (Greiner Bio One). The tube was centrifuged for 30 seconds at 1000 rcf at room temperature to position the separation medium in the tube below the porous barrier.

4 mL of phosphate buffered saline (PBS; without calcium and magnesium) was added to a 15 mL conical tube. Human blood in a 4 mL vacutainer was inverted 10 times to mix the blood. The blood was then added to the conical tube containing the PBS, and the blood and PBS was mixed. The blood and PBS mixture was then poured into the LeucoSep™ tube.

The LeucoSep™ tube was centrifuged at room temperature for 30 minutes at 1250 rcf in a Labnet Centrifuge (or 2100 rpm in a Beckman swinging bucket centrifuge). The enriched cell fraction, containing lymphocytes and peripheral blood mononuclear cells, was collected by pouring off both the plasma supernatant and enriched cell fraction above the porous barrier into a new 15 mL centrifuge tube. The cells were pelleted at 500 rcf for 10 minutes in a Labnet centrifuge (or for 10 minutes at 1100 rpm in a Beckman centrifuge), and the supernatant was discarded.

The pellet was resuspended in 1 mL of freezing media (10% DMSO in heat-inactivated Fetal Bovine Serum). The 1 mL sample was divided into two 0.5 mL aliquots and frozen in a −80° C. freezer. Each 0.5 mL aliquot contained approximately 1,000,000 peripheral blood mononuclear cells.

Example 2. Transducing Peripheral Blood Mononuclear Cells

A 0.5 mL aliquot of peripheral blood mononuclear cells was washed with 0.5 mL of expansion media in placed in a 15 mL conical vial. The cells were pelleted at 250 rcf for 7 minutes, and the supernatant was decanted, leaving approximately 100 µL of media in the tube.

Transduction media was prepared, containing 0.4 mL StemPro-34 Lance Media; 5 hKOS; 5 µL hc-Myc; 3 µL h-Klf4; 2 µL Polybrene in water (1 mg/mL dilution); and Polybrene reagent (10 mg/mL).

Frozen CytoTune virus vials were placed in a 37° C. bath for 8 seconds, causing the reagent to melt, and then placed in a 4° C. cold block. The virus was mixed into the PBMC expansion media.

The transduction media was then placed in the 15 mL conical vial to resuspend the cell pellet. The transduction media and cells were placed in one well of a 24-well plate and incubated overnight at 37° C. in a humidified atmosphere of 5% $CO_2$.

Example 3. Culturing Transduced Cells 1 mL of Geltrex ready-to-use solution was added to each well of a 6-well plate. The plate was incubated at 37° C. and 5% $CO_2$ for 1 hour.

A frozen vial of about 8500 cells in MEF media were thawed in a 37° C. bath for 4 minutes, and the cell solution was transferred into a 15 mL conical tube. 8 mL of pre-warmed Mouse Embryonic Fibroblast (MEF) media was added to the 15 mL tube, and 0.5 mL of MEF media was used to rinse the empty vial into the 15 mL tube. The cell suspension was centrifuged at 250 rcf for 8 minutes, the supernatant was discarded, and the cells were resuspended in 2 mL of MEF media.

The Geltrex was removed from the wells of the 6-well plate, and the cells in MEF media were transferred to the 6-well plate. The cells were cultured at 37° C. in a humidified atmosphere of 5% $CO_2$ for 1 day.

The cells were then cultured in StemPro-34 media, containing penicillin and streptomycin for 3 days at 37° C. in a humidified atmosphere of 5% $CO_2$. The cells were then cultured in iPSC media, containing penicillin and streptomycin for 14 days at 37° C. in a humidified atmosphere of 5% $CO_2$.

Example 4. Differentiating Pluripotent Stem Cells into Hepatocytes

When IPS cell line 1098 became 20 to 40% confluent, the cells were harvested using Versene. Definitive endoderm media A was added to the cells, and the cells were incubated for 1 day. Definitive endoderm media B was then added to the cells, and the cells were incubated for another day. The cells were then incubated in RPMI+B27 media containing BMP-4 and FGF-2 for 5 days. The cells were then incubated with RPMI+B27 media containing hepatocyte growth factor for 5 days. The cells were then incubated with hepatocytes culture media containing Oncostatin for 5 days. Cells and cell culture supernatant were collected for analysis. The cells were then incubated with hepatocytes culture media containing Oncostatin for 10 days, and cells and cell culture supernatant were collected for analysis.

Example 5. Analyzing Hepatocyte Biomarkers

Figure 2:
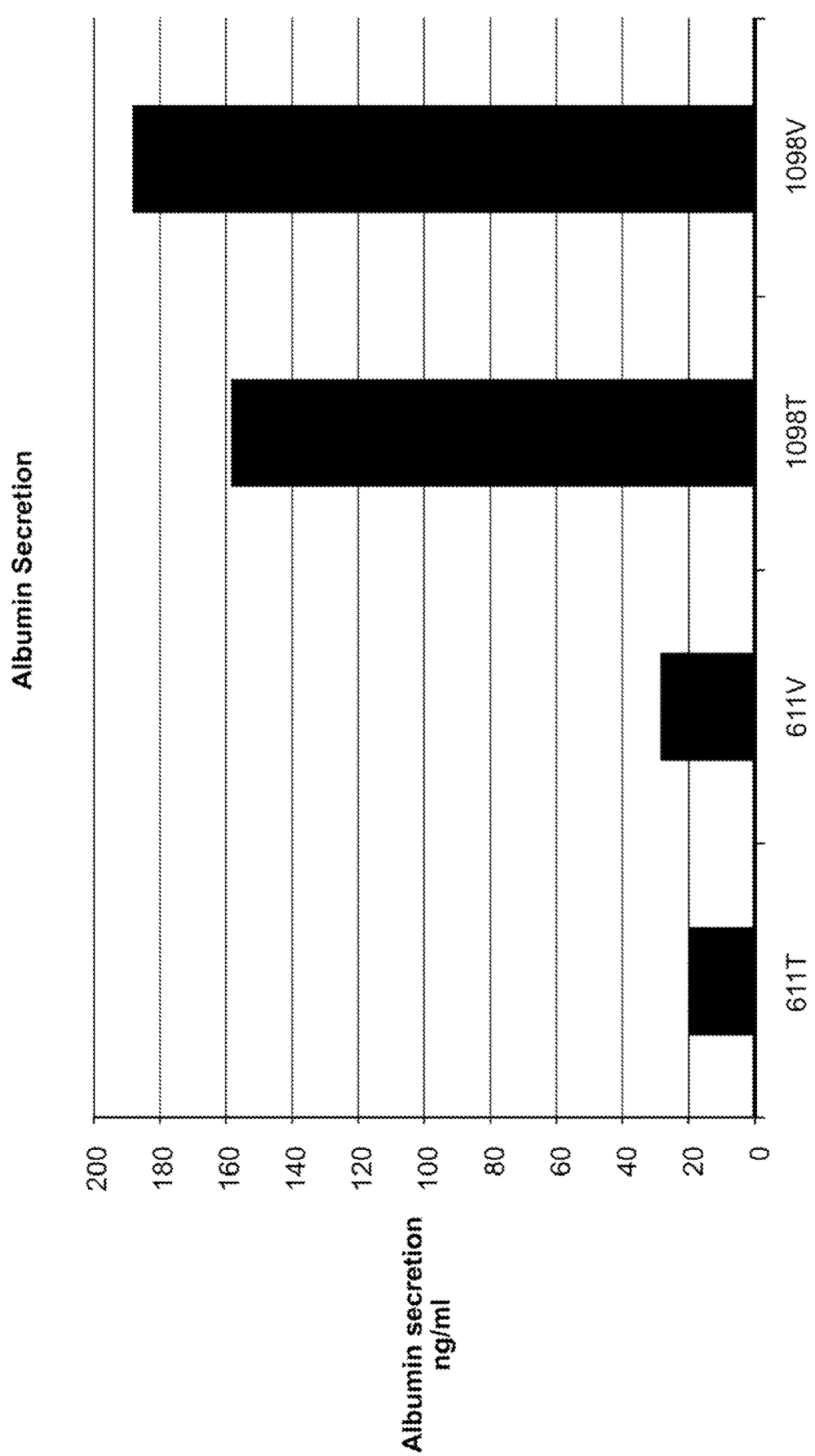
FIG. 2 shows albumin secretion by human IPSC-derived hepatocytes from control human sample (1098) and Parkinson's patient sample (611). Albumin secretion is a well-established functional measure of hepatocytes. Conditioned media was collected after 24 hours and albumin level was measured in the culture media by albumin ELISA.

Hepatocytes derived from a Parkinson's disease patient (611) and a healthy control (1098) were prepared as described in Examples 1-4. Cell samples were prepared for qPCR analysis of mRNA (FIG. 1). Hepatocytes derived from the Parkinson's disease patient (611) expressed less mRNA for antitrypsin, asialoglycoprotein receptor, and hepatocyte nuclear factor 4, than hepatocytes derived from the healthy control (1098). Hepatocytes derived from the Parkinson's disease patient (611) expressed more Kruppel-like factor 4 mRNA than hepatocytes derived from the healthy control (1098). Cell culture supernatant was assayed for albumin using ELISA (FIG. 2). The hepatocyte cell culture supernatant from the Parkinson's disease patient (611) contained less albumin than the hepatocyte cell culture supernatant from the healthy control (1098).

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method for diagnosing or identifying a risk of developing Parkinson's disease, comprising:
providing a peripheral blood mononuclear cell taken from a human subject;
generating a pluripotent stem cell from the peripheral blood monocuclear cell;
differentiating the pluripotent stem cell into a hepatocyte;
measuring the amount of antitrypsin, asialoglycoprotein receptor, hepatocyte nuclear factor 4, and Kruppel-like factor 4 mRNA in the hepatocyte, and the amount of albumin protein secreted by the hepatocyte; and
diagnosing the subject as having Parkinson's disease or identifying the subject as at risk of developing Parkinson's disease if:
(a) the measured amount of antitrypsin, asialoglycoprotein receptor and hepatocyte nuclear factor 4 mRNA is less than that in a hepatocyte derived from a peripheral blood monocuclear cell taken from an individual without Parkinson's disease and then differentiated into the hepatocyte;
(b) the measured amount of Kruppel-like factor 4 mRNA is greater than that in a hepatocyte derived from a peripheral blood mononuclear cell taken from an individual without Parkinson's disease and then differentiated into the hepatocyte; and (c) the measured amount of secreted albumin is less than that of a hepatocyte derived from a peripheral blood monocuclear cell taken from an individual without Parkinson's disease and then differentiated into the hepatocyte.

2. The method of claim 1, wherein a blood sample of the subject is provided and the peripheral blood mononuclear cell is isolated from the blood sample.

3. The method of claim 1, wherein the amount of antitrypsin, asialoglycoprotein receptor, hepatocyte nuclear factor 4, and Kruppel-like factor 4 mRNA in the hepatocyte is measured using PCR.

4. The method of claim 1, wherein the amount of antitrypsin, asialoglycoprotein receptor, hepatocyte nuclear factor 4, and Kruppel-like factor 4 mRNA in the hepatocyte is measured using microarray analysis or sequencing.

5. The method of claim 1, wherein the amount of albumin protein secreted by the hepatocyte is measured using an immunoassay.

6. A method for identifying a therapeutic agent for treating Parkinson's disease, comprising:
  (a) contacting a first hepatocyte with a compound or composition, wherein the first hepatocyte was generated from a peripheral blood mononuclear cell of a human subject with Parkinson's disease;
  (b) measuring the amount of antitrypsin, asialoglycoprotein receptor, hepatocyte nuclear factor 4, and Kruppel-like factor 4 mRNA in the first hepatocyte and the amount of albumin protein secreted by the first hepatocyte;
  (c) comparing the amount of antitrypsin, asialoglycoprotein receptor, hepatocyte nuclear factor 4, and Kruppel-like factor 4 mRNA in the first hepatocyte and the amount of albumin protein secreted by the first hepatocyte with an amount of antitrypsin, asialoglycoprotein receptor, hepatocyte nuclear factor 4, and Kruppel-like factor 4 mRNA in a control hepatocyte and the amount of albumin protein secreted by the control hepatocyte, wherein said control hepatocyte was generated from the peripheral blood mononuclear cell of the human subject with Parkinson's disease but has not been contacted with the compound or composition; and
  (d) identifying the compound or composition as a therapeutic agent for treating Parkinson's disease if:
    (i) the amount of antitrypsin, asialoglycoprotein receptor, and hepatocyte nuclear factor 4 mRNA in the first hepatocyte is greater than the amount of antitrypsin, asialoglycoprotein receptor, and hepatocyte nuclear factor 4 mRNA in the control hepatocyte;
    (ii) the amount of Kruppel-like factor 4 mRNA in the first hepatocyte is less than the amount of Kruppel-like factor 4 mRNA in the control hepatocyte; and
    (iii) the amount of albumin protein secreted by the first hepatocyte is more than the amount of albumin secreted by the control hepatocyte.

7. The method of claim 6, wherein the first hepatocyte is contacted with a compound, and the compound is a small molecule.

8. The method of claim 6, wherein the first hepatocyte is contacted with a composition, and the composition comprises a biologic.

9. The method of claim 8, wherein the biologic is CRISPR/Cas, a zinc finger nuclease, or a transcription activator-like effector nuclease.

* * * * *